US00PP23156P3

(12) United States Plant Patent
Rogmans et al.

(10) Patent No.: US PP23,156 P3
(45) Date of Patent: Oct. 30, 2012

(54) ***LEMNA MINOR* PLANT NAMED 'HENRY BLANKE'**

(50) Latin Name: *Lemna minor*
Varietal Denomination: Henry Blanke

(75) Inventors: Maria Rogmans, Kalkar (DE); Hermann-Josef Wilhelm, Kalkar (DE)

(73) Assignee: Maria Rogmans, Kalkar (DE)

( * ) Notice: Subject to any disclaimer, the term of this patent is extended or adjusted under 35 U.S.C. 154(b) by 0 days.

(21) Appl. No.: 12/801,389

(22) Filed: Jun. 7, 2010

(65) Prior Publication Data

US 2010/0333244 P1 Dec. 30, 2010

(30) Foreign Application Priority Data

Jun. 5, 2009 (QZ) ..... 20090984

(51) Int. Cl.
*A01H 5/00* (2006.01)

(52) U.S. Cl. ..... Plt./342

(58) Field of Classification Search ..... Plt./342, Plt./263.1, 395
See application file for complete search history.

(56) References Cited

OTHER PUBLICATIONS

Earl J.S. Rook; http://www.rook.org/earl/bwca/nature/aquatics/lemna.html; 3 pages; 2002.*

* cited by examiner

*Primary Examiner* — Kent L Bell
(74) *Attorney, Agent, or Firm* — Buchanan Ingersoll & Rooney PC

(57) ABSTRACT

A new *Lemna minor* plant named 'Henry Blanke' is provided. The plant is particularly well suited to serve as a biomass renewable energy source. The plant is small in stature but unlike Dwarf Duckweed possesses short roots which well enable the absorption of nutrients present in water. Such short roots also enable the ready separation of adjoining plants. Strong green leaves are displayed. The plant is well able to maintain active biosynthesis under low light conditions. The plant is particularly well suited to metabolize carbon dioxide from emissions with a simultaneous increase of mass.

2 Drawing Sheets

Botanical/commercial classification: *Lemna minor*/Duckweed cv. Henry Blanke.

BACKGROUND OF THE INVENTION

*Lemna minor* is a member of the Lemnaceae family and is recognized to be a tiny infrequently flowering plant that often grows while floating in still (e.g., ponds) or slowly-moving fresh water. The species occurs throughout the world except in the coldest regions. Such plant commonly is known simply as Duckweed. Plant coloration between green and greenish-brown commonly is observed, while the plant floats as a blanket on the water surface. See the PLANTS Profile for common *Lemna minor* provided by the United States Department of Agriculture, Natural Resources Conservation Service. There the typical and entangled roots of *Lemna minor* are illustrated. In recent years, interest has focused on the use of plants for possible renewable energy source, as well as for industrial utilization. *Lemna minor* plants have been included in this interest.

Such *Lemna minor* plants are generally adapted to produce carbohydrates through the mixotropic conversion of carbon dioxide while deriving nourishment via both autotropic and heterotropic mechanisms. For instance, organic matter (even contamination and waste) present in water and carbon dioxide from the air can be combined by the tiny plants. Carbohydrates in the water are broken down into simple sugars. During growth phosphorus and nitrogen are consumed. Unwanted substances are removed from the water. Upon harvest, the resulting plants can be burned directly to yield a source of fuel or energy. Alternatively, the plants can be processed to form a biofuel wherein the plants serve as a feedstock for ethanol or methane production. Less reliance upon fossil fuels is required upon the utilization of such energy source. The plant further serves as a natural water purifier.

It is recognized that a profuse root formation provides floating Duckweed plants with the ability to well receive nutrients present in water during biosynthesis. However, common *Lemna minor* plants are recognized to possess such an extensive production of long and entangled roots that efficient planting and harvest is complicated. This plant morphology has been found to interfere with commercially viable large scale biomass production. The plants also commonly also require culture while utilizing relatively high light conditions.

When common Dwarf Duckweed (i.e., *Wolffia arrhiza*) is considered for biomass production, it is found that such plants can be readily separated from one another since the plants are completely rootless. However, such absence of roots manifests a decreased ability to absorb nutrients from water even in the presence of high light conditions. Accordingly, photosynthesis proceeds at a diminished rate in such species when compared to that of common *Lemna minor*.

SUMMARY OF THE INVENTION

A combination of naturally-occurring crossing and extensive selection was utilized to form the new *Lemna minor* plant of the present invention in the absence of genetic engineering and intentional chemically-induced mutagenesis. Naturally-occurring *Lemna minor* plants from diverse natural sources were admixed in a common water compartment. The plants were provided in well water that was rich in iron together with fertilizer. Reduced pulsating light was directed towards the plants in order to encourage blossoming and naturally-occurring cross-fertilization among the randomly present plants in the water compartment. The contents of the water compartment were subjected to gentle stirring in order to promote random crossing among the plants. Next the plants were subjected to a reduced light source of no more than 50 Lux. Under such conditions the number of living plants was greatly reduced. In a following step the light source was even further reduced to an extremely low level of no more than 20 Lux. Thereafter only a few *Lemna minor* plants were still living and each was found to be physically and biologically different from each other. From among the surviving plants a single plant of the new variety of the present invention that thrived under such low light conditions was selected and was carefully preserved.

The new plant of the present invention was found to display the following combination of characteristics:

(a) is small in size with a large effective surface per volume and is particularly well-suited to serve as a biomass renewable energy source, (b) possesses readily-separable short roots which well enable the absorption of nutrients, (c) possesses strong green coloration, and (d) is well adapted to maintain active biosynthesis under low light conditions.

The plant is particularly well-suited to metabolize carbon dioxide from emissions with a simultaneous increase in mass. Also, nourishment can be derived from substances present in the water, including water contaminants.

The propensity for the new plant to grow and to increase in mass is particularly noteworthy. The small plant size enables the presence of a large number of individual plants in a given production area. As the plants spontaneously asexually reproduce at a high growth rate, the resulting mass is rapidly enlarged. The ability of the adjoining short roots to be separated enables efficient harvest and handling in the absence of severe entanglement and clumping. Additionally, the root structure nevertheless is sufficient for the efficient absorption of nutrients from water. Such efficiency is evidenced by a strong green coloration that is facilitates the conduct of productive photosynthesis even under reduced light conditions. Initially, carbon dioxide is removed from the atmosphere and is bound and thereafter chemical components are extracted from the water. The plants contain high protein and high carbohydrate concentrations and are produced at a rapid growth rate. As carbon dioxide is captured from the atmosphere, global warming concerns are diminished, and water quality is improved. Periodic regular harvesting ensures a continuous new supply of new young plants.

The new variety of the present invention has been asexually reproduced at Kalkar, Germany, and at Naktiunbouw, The Netherlands. Such asexual reproduction takes place spontaneously as tiny buds are formed in a meristematic zone, become unattached from a mother plant, and grow to form a new identical plant. It has been found that the new variety particularly well undergoes asexual propagation under low light conditions when grown in well water that is rich in iron. The new variety undergoes such asexual reproduction via this route in a true-to-type manner.

The new plant has been named 'Henry Blanke.'

DESCRIPTION OF THE PHOTOGRAPHS

The accompanying photographs illustrate typical plants and plant parts of the new variety of the present invention. The plants were being grown at Kalmar, Germany. It is apparent from the photographs that the plants of the new variety are extremely small in size. Accordingly, the photographs are intended to depict plants of the new variety as completely as is reasonably possible for subject matter of this nature.

FIG. 1 illustrates from above a relatively homogenous population of *Lemna minor* plants of the new variety while floating on a water surface. Included are a few *Azolla caroliniana*, sometimes known as Duckweed Fern, Such *Azolla* plants were providing some nitrogen to the culture medium. The presence of such *Azolla* plants, however, is non-essential, and the new variety can be well cultivated in the absence of such *Azolla* plants.

DETAILED DESCRIPTION

The chart used in the identification of colors is that of The Royal Horticultural Society (R.H.S. Colour Chart), London, England (1995 Edition or equivalent). The plants were grown at Kalmar, Germany, and at Naktiunbouw, The Netherlands.

Botanical classification: *Lemna minor,* cv. 'Henry Blanke'.

Growth habit: Floats freely on the surface of still or slowly moving water.

Figure 1:
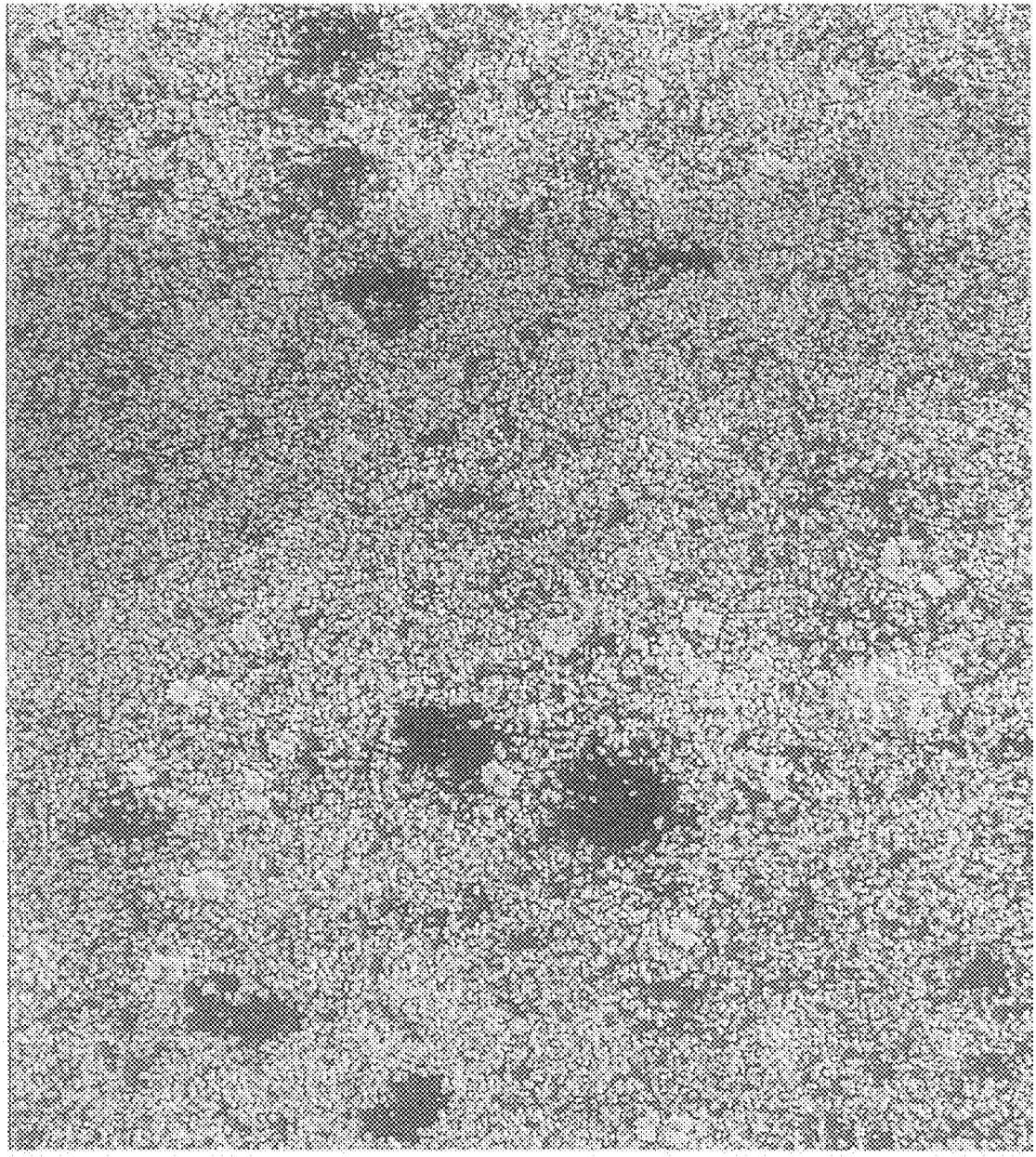
Figure 2:
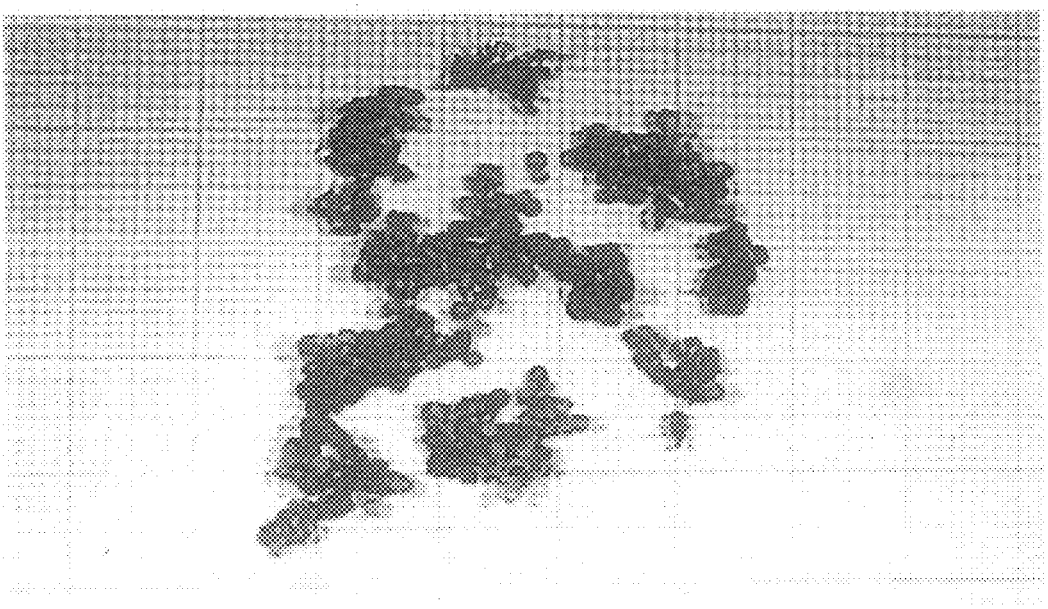
FIG. 2 illustrates individual plants and small clusters of *Lemna minor* plants of the present invention when removed from water and present on a one-millimeter square grid for size comparison. Such plants can be readily separated from one another in view of the presence of atypical short roots which well resist entanglement among adjacent roots.
Figure 3:
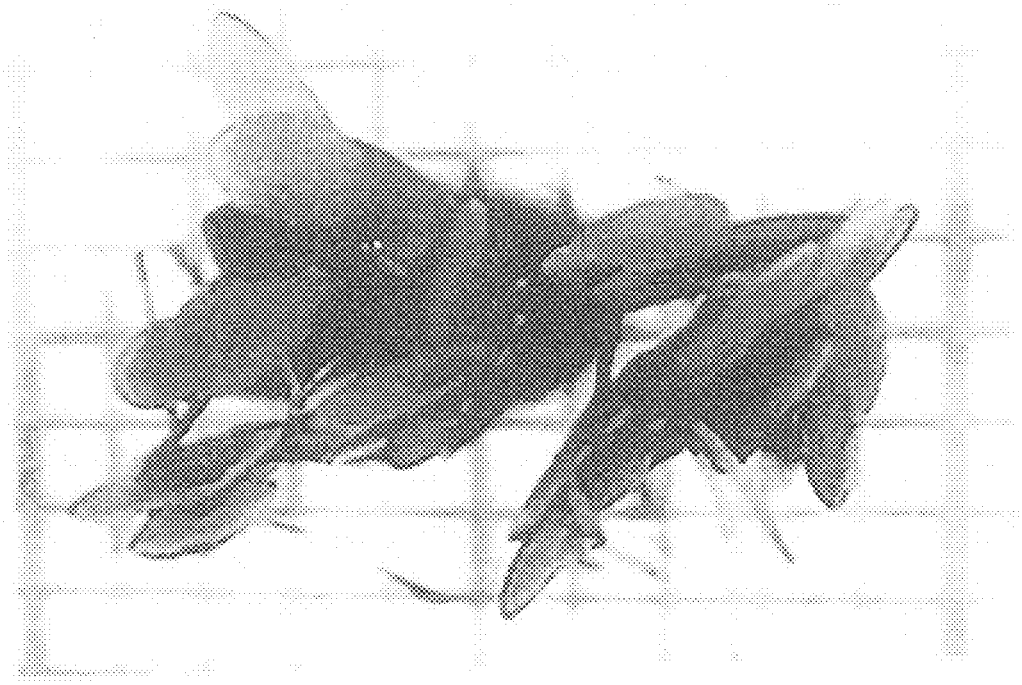
FIG. 3 illustrates an enlarged view of the representative leaves and the representative atypical short roots of the new variety of the present invention. A one-millimeter square grid is included for size comparison.

Plant characteristics: Extremely small in size. Unlike those commonly displayed by the species, the green roots are atypically short and are substantially untangled. The roots, as illustrated in FIG. 3, are relatively straight and commonly have lengths of only 1.5 to 2 mm. This can be compared to considerably longer root lengths exceeding 5 mm typically exhibited by the species. Such root character well resists entanglement unlike the roots commonly observed in the species. The short root length of the new variety nevertheless has been found to well support abundant plant growth. Accordingly, plants of the new variety can be readily harvested without experiencing handling complications created by root entanglement whereby adjoining plants become securely attached to one another. Each plant forms short to medium ovate to round leaves having a length of approximately 1.5 to 2 mm, or more, arranged along a main axis or shoot. The leaves commonly display a lesser width at the widest point than length. Leaves having a near round or circular configuration sometimes are observed. The upper surfaces of the leaves commonly are near Yellow-Green Group 144A in coloration, and the under surfaces commonly are darker and approach Green Group 141A in coloration. Anthocyanin coloration commonly is absent on both surfaces of the leaves and when present is very slight and very weak in its presentation. The leaf apex is rounded and the leaf margin is entire. Upon exposure to light under growing conditions that promote flowering isolated barely visible flowers are formed.

Since the new plant is customarily grown under conditions which suppress flowering, no inflorescence is available for inspection. However, when flowering occurs based upon available information, the resulting flowers are believed to be typical of the species.

Low light tolerance: The new plant is remarkable in its ability to grow and to carry out photosynthesis even under low light conditions. When grown in a medium that is rich in iron, the new variety has been found to display the ability to absorb iron in an optimum amount that promotes advantageous growth. A high tolerance and utilization of carbon dioxide is displayed. Unwanted carbon dioxide from emissions is well metabolized. A high plant mass is produced under even low light conditions.

Asexual propagation: The plant readily self doubles through spontaneous asexual reproduction involving plant division. Buds form in a meristematic zone, become unattached from a mother plant, and thereafter form a new plant of the same phenotype and genotype. The plants of the new variety can efficiently be grown to form a biomass under relatively low light conditions (e.g., 500 to 1,000 Lux) in a stacked system of bioreactors that are provided in a plurality of layers. Under such conditions sexual reproduction is suppressed and asexual reproduction spontaneously progresses to form an ever increasing biomass of the new variety on an expeditious basis. Periodic harvesting is carried out as the bioreactors reach maximum capacity.

The invention claimed is:

1. A new and distinct *Lemna minor* plant, substantially as illustrated and described.

* * * * *